May 20, 1975 P. J. MURISON Plant Pat. 3,721
POINSETTIA PLANT
Filed March 20, 1974
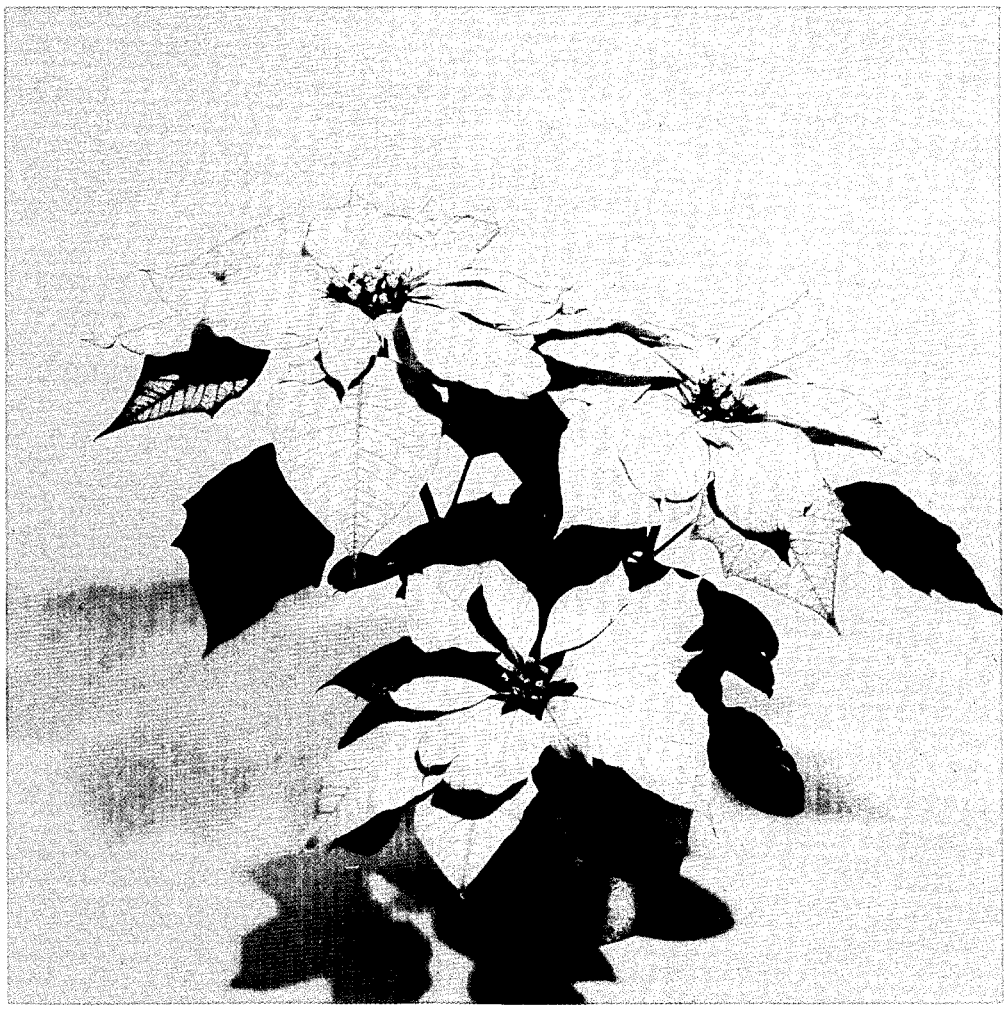

United States Patent

Plant Pat. 3,721
Patented May 20, 1975

3,721
POINSETTIA PLANT

Peter J. Murison, Hoddesdon, England, assignor to Mikkelsens Inc., Ashtabula, Ohio Filed Mar. 20, 1974, Ser. No. 453,056
Int. Cl. A01h 5/00
U.S. Cl. Plt—86 1 Claim The present invention relates to a new and distinctive cultivar of poinsettia plant known by the varietal name Mikkel Fantastic, and botanically known as *Euphorbia pulcherrima.*

The new cultivar is a sport of Mikkel Pink Rochford, an unpatented cultivar, and the new cultivar was discovered in a greenhouse in Hoddesdon, Herts, England, amid flowering plants of the parent cultivar. The parent cultivar Mikkel Pink Rochford is a sport of the unpatented cultivar Mikkel Rochford, which is in turn a sport of the well-known commercial cultivar Paul Mikkelsen, disclosed in U.S. Plant Pat. No. 2,328.

The new cultivar has been asexually reproduced by cuttings both in Hoddesdon, Herts, England, at Rochfords Nurseries, and in the greenhouses of Mikkelsens Inc., Ashtabula, Ohio, and has been found to retain its distinctive characteristics through successive propagations.

The following characteristics distinguish the new cultivar from its parent and from other poinsettias commercially known and used in the floriculture industry:

1. A distinct deep pink coloring of the bracts, a deeper pink compared to the bract color of the parent cultivar, thereby providing a color suitable for offseason flowering.
2. Easy to propagate.
3. More vigorous growth habit than parent.
4. Breaks well when pinched; apical dominance is destroyed thereby forming a well branched, full plant thus reducing the number of young plants needed to produce a crop.
5. Foliage is a somewhat darker green than parent cultivar.

The accompanying colored photographic drawing illustrates the overall appearance of the new cultivar, with the colors being as true as possible to obtain in color reproductions of this type.

The following is a detailed description of the new cultivar based on plants produced under commercial practices in the greenhouses of Mikkelsens Inc., Ashtabula, Ohio. Color references are to the Royal Horticultural Society Colour Chart except where general color terms of ordinary dictionary significance are used.

Parentage: Sport of Mikkel Pink Rochford.
Form of plant: Upright, well branched.
Growth habit: Medium vigor; branches well when terminal tip is removed when plant is in vegetative condition.

Rooting: Quite rapid, with roots being more fibrous than Paul Mikkelsen.
Blooming habit: Typical of poinsettias in which terminal leaves change to color described and an involucre develops with the cyathia; responds to photoperiodic treatment.
Blooming season: Natural flowering late November or early December; can be forced on 11 hour daylength at 62°–64° F. in nine weeks.
Foliage:
- *Size.*—Medium.
- *Quantity.*—Normal for this type of poinsettia.
- *Color.*—New foliage—upper side—near 137B; under side—near 139C. Old foliage—upper side—139A; under side—138B.
- *Shape.*—Nearly obovate and slightly crenate, with the tips being quite pointed.
- *Texture.*—Upper side—glossy and glabrous; under side—rough with veins protruding.
- *Edge or margin.*—Slightly crenate.
- *Aspect.*—Nearly horizontal, with petiole at slight angle.
- *Disease resistance.*—Good resistance to botrytis and root rot organisms, when compared to susceptible varieties in same growing environment.

Flowers: (Cyathia).
- *Borne.*—On strong, medium length stems and in clusters of several on stem.
- *Quantity.*—Moderate in greenhouse.
- *Continuity.*—Blooms in one season, having a permanence of several months.
- *Buds.*—The first visible cyathia appear with red cup, round and on short stems. Cyathias are typically in groups of threes.
- *Bracts.*—Appear alternately with some whirl with close internodes; form, obovate to obtuse; texture, smooth with veining less obvious than on parent cultivar; overall color appearance dark pink toward rose red. Color: top—red 50B. Under—red 51C.
- *Reproductive organs.*—Stamens: Color, deep yellow. Pollen: Color, yellow 12. Styles: Red 45A. Ovaries: Green 143C.

I claim:

1. A new and distinct cultivar of poinsettia characterized particularly by its distinct deep pink coloring of the bracts; ease of propagation; ability to break well when pinched thereby forming a well branched, full plant, and by is dark green foliage.

No references cited.

ROBERT E. BAGWILL, Primary Examiner